United States Patent [19]

Rajappa et al.

[11] 4,150,229
[45] Apr. 17, 1979

[54] 2,5-DI-(ω-AMINOALKYL-1′)-PYRAZINES

[75] Inventors: Srinivasachari Rajappa, Bombay, India; Helmut Zondler, Bottmingen, Switzerland

[73] Assignee: Ciba-Geigy Corporation, Ardsley, N.Y.

[21] Appl. No.: 864,361

[22] Filed: Dec. 27, 1977

[30] Foreign Application Priority Data

Jan. 7, 1977 [CH] Switzerland ............................ 171/77

[51] Int. Cl.² ............................................ C07D 241/12
[52] U.S. Cl. .................................................. 544/336
[58] Field of Search .................. 260/250 BN; 544/336

Primary Examiner—Jose Tovar

Attorney, Agent, or Firm—Vincent J. Cavalieri; Joseph F. DiPrima

[57] ABSTRACT

2,5-di-(ω-aminoalkyl-1′)-pyrazines are obtained by catalytic hydrogenation of nitro compounds of the formula

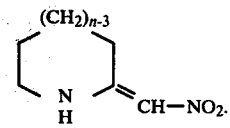

They are suitable as hardeners for epoxides or for the manufacture of polyamides.

12 Claims, No Drawings

2,5-DI-(ω-AMINOALKYL-1')-PYRAZINES

The invention provides 2,5-di-(ω-aminoalkyl-1')-pyrazines which contain 3 to 6 CH$_2$ groups in the alkyl moieties and the process for the manufacture of these compounds.

2,5-Di-(ω-aminoalkyl-1')-pyrazines have hitherto not been known. The structure of these diamines is of such immediate interest to those skilled in the art of polyamide and polyurethane chemistry that the provision of such compounds satisfies a genuine need and constitutes an advance in the art.

It has now been found that 2,5-di-(ω-aminoalkyl-1')-pyrazines can be obtained in simple manner by the catalytic hydrogenation of nitro compounds of the general formula II

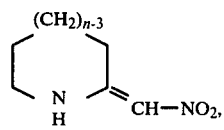

wherein n is an integer from 3 to 6. The success of this synthesis was not to be anticipated, since what was actually to be expected was the formation of the amino compound corresponding to the structure of formula II with retention of the heterocyclic ring. Surprisingly, however, during the hydrogenation a rearrangement accompanied by disintegration of the heterocyclic ring system occurs with simultaneous formation of the pyrazine ring, as illustrated by the following reaction scheme:

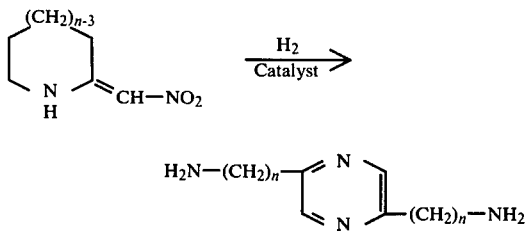

The invention accordingly provides 2,5-di-(ω-aminoalkyl-1')-pyrazines of the formula (I) above, wherein n is an integer from 3 to 6 and the process for the manufacture of these compounds. This process comprises 1. catalytically hydrogenating a nitro compound of the formula II in the presence of an organic acid, optionally in the presence of an additional organic solvent,
2. thereafter removing the catalyst from the reaction mixture by filtration, and
3. isolating the pure end product from the filtrate, if appropriate after temporarily converting it into the salt of a mineral acid.

A preferred embodiment of the invention comprises 2,5-di-(ω-aminoalkyl-1')-pyrazine of the formula I, wherein n is 5, namely of 2,5-di-(5-aminopentyl-1')-pyrazine. This diamine can be obtained in good yield by hydrogenating 2-nitromethene-perhydroazepine.

A further preferred embodiment of the invention comprises the 2,5-di-(ω-aminoalkyl-1')-pyrazine of the formula I, wherein n is 3, namely 2,5-di-(3-aminopropyl-1')-pyrazine. This compound is obtained according to the invention by hydrogenating α-(2-azolidinylidene)-nitromethane.

As organic acids for the manufacture of these diamines by the process of the present invention, there are preferably used aliphatic monocarboxylic acids which contain altogether 2 to 5 carbon atoms, in particular acetic acid. Aliphatic alcohols, for example methanol and isopropanol, are particularly suitable as additional organic solvents. Further suitable solvents are cyclic ethers, such as dioxane and tetrahydrofurane and aromatic solvents. It is also possible to use corresponding solvent mixtures.

The hydrogenation is preferably carried out at temperatures of 20° to 150° C. and at slight overpressure, preferably up to 10 atmospheres. Known nickel, cobalt or noble metal catalysts, such as platinum, palladium, rhodium or ruthenium, are used as hydrogenation catalysts.

The working up of the hydrogenation solution is accomplished by the methods commonly known in the art, where the product of the formula I is isolated either as salt or as free amine. To obtain the mineral salts of the formula I the reaction mixture is concentrated while adding a mineral acid or the mineral acid is added after the bulk of the organic acid used as solvent has been removed. The pure salts are then obtained by recrystallisation. The pure free amine can then be obtained from the aqueous solution of its purified salt by adding a sufficient amount of NaOH or KOH and by extraction with organic solvents. However, the hydrogenation solution can also be worked up directly, avoiding the isolation of the amine salt, with NaOH or KOH to give the crude amine. A further purification by distillation is possible.

The nitro compounds of the formula II, which are the starting materials for the diamines of the present invention, can be obtained by a known method of R. G. Glushkov and O. Yu. Magidson, which is described in Zhur. Obshchei Khim. 30, 1855–60 (1960) and in CA 55, 7430i. ε-Caprolactam for example, is used as starting material for obtaining 2,5-di-(5-aminopentyl-1')-pyrazine. The corresponding lactim methyl ether is prepared first using dimethyl sulphate. The desired 2-nitromethene-perhydroazepine can be obtained therefrom by treatment with nitromethane.

Correspondingly, pyrrolidone-(2) is used as starting material to obtain 2,5-di-(3-aminopropyl-1')-pyrazine and the corresponding α-(2-azolidinylidene)-nitromethane is obtained by means of the above described reaction method.

It will be readily understood by those skilled in the art that the customary reaction products of amines, such as amides, ureas, thioureas, guanidines, biguanidines, amidines and piperazines, can be obtained in known manner from the diamines of the present invention of the formula I.

The diamines of this invention can be used in particular for manufacturing polyamides of the nylon 66 type and polyurethanes. The diamines of the present invention are also suitable as hardeners for epoxide compounds, when the procedure is in general as follows. To 100 g of liquid bisphenol-epoxide resin are added at 60° to 70° C. approx. 30 to 40 g of 2,5-di-(5-aminopentyl-1')-pyrazine. Crosslinking subsequently takes place over the course of several hours at temperatures between 80° and 150° C. (e.g. 15 hours at 140° C.).

MANUFACTURING EXAMPLES

EXAMPLE 1

80 g of 2-nitromethene-perhydroazepine are dissolved in 800 ml methanol and 80 ml of glacial acetic acid and hydrogenated at 45° C. under normal pressure in a shaking vessel in the presence of 16 g of 10% palladium/charcoal. The uptake of hydrogen ceases after approx. 3 to 4 hours. The catalyst is filtered off and then 2 equivalents of alcoholic hydrochloric acid are added to the filtrate. After concentration in vacuo the resulting solid residue is dissolved in benzene and concentrated to dryness once more. The solid residue is recrystallised once from 100 ml of isopropanol and thereafter from a mixture of methanol and isopropanol. Yield: 55.5 g (67% of theory) of 2,5-di-(5-aminopentyl-1')-pyrazine-hydrochloride; m.p. 305° C. Titration of the salt with NaOH confirms the presence of the dihydrochloride.

Conversion into the free base is accomplished by dissolving 150 g of dihydrochloride in 600 ml of 5 N sodium hydroxide solution. Extraction is effected with chloroform, the extract is dried with anhydrous potassium carbonate and concentrated by rotary evaporation in vacuo at 50° C. to yield 121.3 g of crystalline amine. Distillation yields 101 g of pure 2,5-di-(5-aminopental-1')-pyrazine with a boiling point of 150° C. at 0.02 Torr and a melting point of 58°–61° C.

The NMR spectrum is deuterised dimethyl sulphoxide shows the structure: 8.25 ppm singlet (2 aromatic hydrogen atoms); 2.3 to 2.9 ppm multiplet (2 $CH_2$ groups in the pyrazine ring and 2 $CH_2$ groups adjacent to the amino groups); 1.0 to 2.0 multiplet (6 $CH_2$ groups); 1.65 singlet (2 $NH_2$ groups). Mass spectrum: m/e=250 (M+); 233 (M+—$NH_3$); 221 (M+—$CH_2NH$); 30 ($CH_2=NH_2^+$).

EXAMPLE 2

312 g (2 moles) of crude 2-nitromethene-perhydroazepine are dissolved in 680 g of isopropyl alcohol. After addition of 10 g of 5% palladium/charcoal suspended in 132 g of glacial acetic acid, hydrogenation is effected at 90° C. under a hydrogen pressure of 8 bar. The theoretical amount of hydrogen (112 liters) is taken up after 2 hours. The reaction mixture is cooled to room temperature and the catalyst is filtered off. The catalyst is washed with 150 g of isopropyl alcohol. To the greenish-yellow solution are added 88 g of powdered sodium hydroxide and the mixture is kept for 16 hours under reflux (78° C.) The sodium acetate which has formed is filtered off at room temperature and the reaction mixture is washed with isopropyl alcohol. After the solvent has been removed at 85° C./14 Torr, the turbid, greenish-brown oil is distilled over a distillation bridge at 0.1 Torr. The 2,5-di-(5-aminopentyl-1')-pyrazine distills at 167°–176° C. The yield is 141.5 g (i.e. 56.6% of theory). The product has a melting point of 55°–58° C.

EXAMPLE 3

A solution of 10 g of the 2-nitromethane perhydroazocine in a mixture of 100 ml methanol and 10 ml acetic acid is hydrogenated at 45° at 1 atm. pressure in presence of 2 g of 10% Pd/C catalyst. After the reduction is complete, the solution is filtered from the catalyst, treated with the required amount of isopropanolic hydrochloric acid and evaporated in vacuo. The residue is treated with benzene and again evaporated to remove any moisture. Isopropanol is then added and the solid that separates is filtered after some time. It is recrystallised from a mixture of methanol and isopropanol to give 2,5-di(6-aminohexyl-1')pyrazine dihydrochloride melting at 288°–289° (d).

EXAMPLE 4

A solution of 8 g of the 2-nitromethene piperidine in a mixture of 100 ml methanol and 8 ml acetic acid is hydrogenated at 45° at 1 atm. pressure in presence of 1.6 g of 10% Pd/C catalyst. After the reduction is complete, the solution is filtered from the catalyst, treated with the required amount of isopropanolic hydrochloric acid and evaporated in vacuo. The residue is treated with benzene and again evaporated. The residual gummy hydrochloride is boiled several times with isopropanol and the solvent decanted off. The residue is dissolved in methanol, treated with isopropanol and left at room temperature for three days. The crystals are collected and, if necessary, recrystallised from a mixture of methanol and isopropanol to give 2,5-di(4-aminobutyl-1')pyrazine dihydrochloride melting at 305°–309° (d).

We claim:

1. A 2,5-di-(ω-aminoalkyl-1')-pyrazine of the formula I

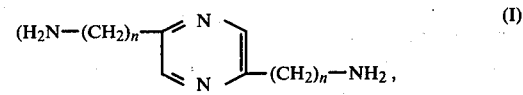

in which n is an integer from 3 to 6.

2. A 2,5-di-(ω-aminoalkyl-1')-pyrazine according to claim 1, wherein n is 5.

3. A 2,5-di-(ω-aminoalkyl-1')-pyrazine according to claim 1, wherein n is 3.

4. A process for the manufacture of 2,5-di-(ω-aminoalkyl-1')-pyrazine according to claim 1, in which
  1. a nitro compound of the formula II

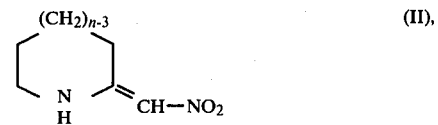

wherein n is an integer from 3 to 6, is catalytically hydrogenated in the presence of an aliphatic monocarboxylic acid having 2 to 5 carbon atoms,
  2. the catalyst is thereafter removed from the resultant mixture by filtration, and
  3. the pure end product is isolated from the filtrate.

5. A process according to claim 4, wherein the aliphatic monocarboxylic acid is glacial acetic acid.

6. A process according to claim 4, wherein the hydrogenation is carried out in the presence of an additional organic solvent selected from the group consisting of an aliphatic alcohol, a cyclic ether, an aromatic solvent or mixtures thereof.

7. A process according to claim 4 wherein the hydrogenation is carried out at temperatures of 20° to 150° C.

8. A process according to claim 4, wherein the hydrogenation is carried out at normal pressure or at slight overpressure.

9. A process according to claim 4, wherein the hydrogenation is carried out in the presence of known nickel, cobalt or noble metal catalysts.

10. A process according to claim 4, wherein 2-nitrometheneperhydroazepine is used as nitro compound of the formula II.

11. A process according to claim 4, wherein α-(2-azolidinylidene)-nitromethane is used as nitro compound of the formula II.

12. A process according to claim 4 wherein the pure end product is isolated from the filtrate after temporary conversion into the salt of a mineral acid.

* * * * *